United States Patent [19]

Morgan et al.

[11] Patent Number: 4,748,153

[45] Date of Patent: May 31, 1988

[54] COMPOUNDS HAVING SOMATOSTATIN-LIKE ACTIVITY USEFUL AS LOCAL ANTI-INFLAMMATORY AGENTS

[75] Inventors: Evan R. Morgan, Bridgewater, N.J.; Daniel F. Veber, Ambler, Pa.; Sanford L. Steelman, Watchung, N.J.

[73] Assignee: Merck & Co., Inc., Rahway, N.J.

[21] Appl. No.: 92,352

[22] Filed: Sep. 2, 1987

Related U.S. Application Data

[63] Continuation of Ser. No. 847,349, Apr. 2, 1986, abandoned, which is a continuation-in-part of Ser. No. 728,019, Apr. 29, 1985, Pat. No. 4,585,755.

[51] Int. Cl.$^4$ ............................................. A61K 37/02
[52] U.S. Cl. ........................................ 514/10; 514/11; 514/806
[58] Field of Search ............................ 514/10, 11, 806

[56] References Cited

U.S. PATENT DOCUMENTS

| | | |
|---|---|---|
| 4,235,886 | 11/1980 | Freidinger et al. .................. 514/11 |
| 4,310,518 | 1/1982 | Freidinger et al. .................. 514/11 |
| 4,505,897 | 3/1985 | Coy et al. ............................ 514/11 |
| 4,522,813 | 6/1985 | Nutt .................................... 514/11 |
| 4,585,755 | 4/1986 | Morgan et al. ...................... 514/11 |

Primary Examiner—J. R. Brown
Assistant Examiner—F. T. Molzie
Attorney, Agent, or Firm—Salvatore C. Mitri; Michael C. Sudol; Mario A. Monaco

[57] ABSTRACT

Compounds having somatostatin-like activity have been found to be useful as local anti-inflammatory agents in the treatment of such conditions as, for example, psoriasis, eczema, seborrhea, and other localized inflammatory and allergic conditions. Particularly useful are cyclic and bridged somatostatin analogs.

4 Claims, No Drawings

COMPOUNDS HAVING SOMATOSTATIN-LIKE ACTIVITY USEFUL AS LOCAL ANTI-INFLAMMATORY AGENTS

This application is a continuation of application Ser. No. 847,349 filed Apr. 2, 1986, now abandoned which, in turn, is a continuation-in-part of application Ser. No. 728,019 filed Apr. 29, 1985, now U.S. Pat. No. 4,585,755, published Apr. 29, 1986.

BACKGROUND OF THE INVENTION

This invention relates to the use of compounds having somatostatin-like activity as local anti-inflammatory agents for the treatment of inflammatory and allergic conditions such as, for example, psoriasis, eczema, seborrhea, and the like.

Particularly useful are known cyclic and bridged cyclic somatostatin analogs such as are disclosed and described in U.S. Pat. Nos. 4,310,518 and 4,235,886, in Belgian Pat. No. 85018747, in European Application No. 83,111,747.8, and by D. Sarantakis, et al. [FEBS Letters, 92, 153–155 (1978)]. In these U.S. Patents, the Belgian Patent, the European Patent Application, and the Sarantakis, et al. publication these compounds are stated to be capable of inhibiting the release of glucagon, insulin, and growth hormone and reducing gastric secretions.

DESCRIPTION OF THE INVENTION

It has now been found that inflammatory and allergic conditions such as, for example, psoriasis, eczema, seborrhea, and the like, as well as atopic diseases affecting the eye such as hay fever, kerato conjunctivitis, vernal conjunctivitis, and other ocular diseases where immunological reactions to allergies are appropriate, can be treated by local; e.g., topical, application with compounds that have somatostatin-like activity and, in particular, those compounds disclosed and described in U.S. Pat. Nos. 4,310,518 and 4,235,886, in Belgian Pat. No. 85018747, in European Patent Application No. 83,111,747.8, and by the D. Sarantakis, et al. publication.

Therefore, this invention is directed in general toward the use of compounds having somatostatin-like activity and, in particular, the cyclic and bridged cyclic somatostatin analogs disclosed and described in U.S. Pat. Nos. 4,310,518 and 4,235,886, in Belgian Pat. No. 85018747, in European Patent Application No. 83,111,747.8, and by the D. Sarantakis, et al. publication for locally treating inflammatory and allergic conditions. These cyclic and bridged cyclic somatostatin analogs and the methods for their preparation disclosed and described in U.S. Pat. Nos. 4,310,518 and 4,235,886, in Belgian Pat. No. 85018747, in European Patent Application No. 83,111,747.8, and by D. Sarantakis, et al. [FEBS Letters, 92, 153–155 (1978)] are incorporated herein by reference.

Thus, the general class of cyclic and bridged cyclic somatostatin analog compounds that can be used to locally treat inflammatory and allergic conditions according to this invention are those having the general formulae:

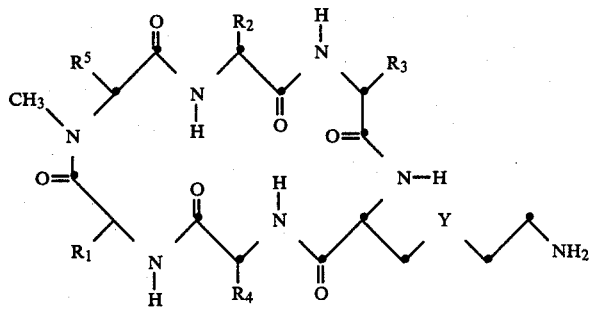

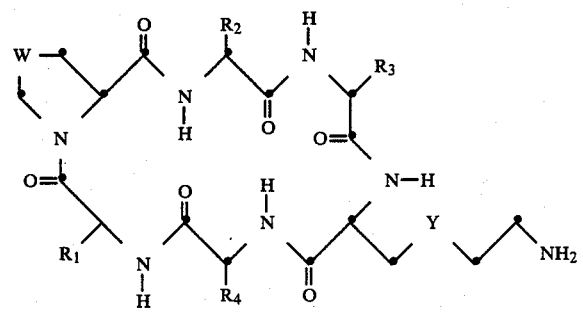

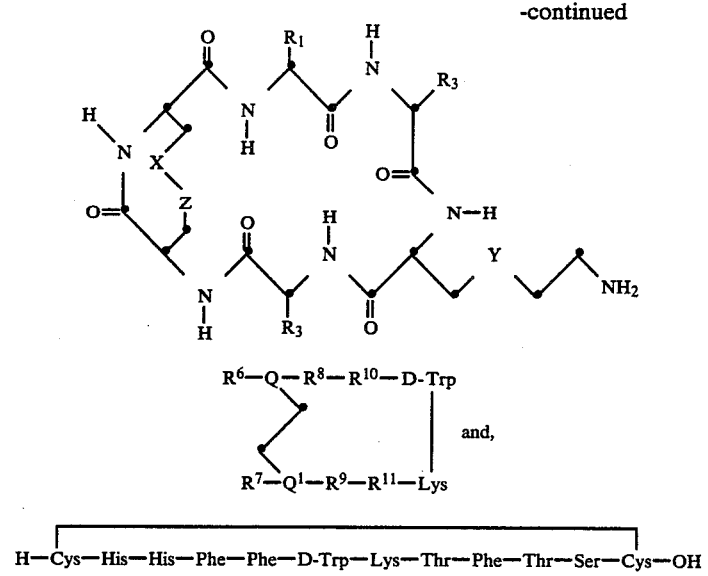

-continued

III

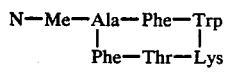

IV and,

V

H—Cys—His—His—Phe—Phe—D-Trp—Lys—Thr—Phe—Thr—Ser—Cys—OH wherein in each of the compounds of Formulae I, II and III:

W is S or (CH$_2$)$_n$ wherein n is 0, 1, or 2;

X and Z are S or CH$_2$ provided that at least one of X or Z is S;

Y is S or (CH$_2$)$_m$ wherein m is 0, 1 or 2 such that the sulfur may be in any position along the chain;

R$_1$ and R$_2$ are independently loweralkyl, benzyl, substituted benzyl where the substituent may be one or two of loweralkyl, halogen, hydroxy, amino, nitro or loweralkoxy; and loweralkyl substituted with a 5- or 6-membered heterocyclic ring;

R$_3$ is 3-indolylmethyl or substituted 3-indolylmethyl wherein the substituent may be loweralkyl, loweralkoxy, or halogen;

R$_4$ is loweralkyl, hydroxyloweralkyl, benzyl, carboxyloweralkyl, aminoloweralkyl or substituted benzyl wherein the substituent may be loweralkyl, loweralkoxy, hydroxy, halogen, amino or nitro; and R$_5$ is loweralkyl, benzyl, or substituted benzyl wherein the substituent is loweralkyl, loweralkoxy, hydroxy, halogen amino or nitro;

and wherein in the compound of Formula IV:

R$^6$ is D-Phe; CH$_3$(CH$_2$)$_8$CO-D-Phe; or is absent;

R$^7$ is Thr or is absent;

R$^8$ and R$^9$ can each independently be Phe or be absent;

R$^{10}$ is Phe or Tyr;

R$^{11}$ is Val or Thr;

Q is Cys or Asn; and,

Q$^1$ is Cys or, when Q, R$^6$ and R$^7$ are absent, Gaba.

In the Formulae I, II and III compounds, the term "loweralkyl" represents those alkyl groups either straight or branched chain, which have from 1-5 carbon atoms. Examples of such alkyl groups are methyl, ethyl, propyl, iso-propyl, butyl, sec-butyl, pentyl and the like.

The term "loweralkoxy" represents those alkoxy groups of from 1-5 carbon atoms, in either a straight or branched chain. Examples of such alkoxy groups are methoxy, ethoxy, propoxy, isopropoxy, butoxy, tert-butoxy, pentoxy and the like.

The term "halogen" or "halo" represents fluorine, chlorine, bromine and iodine.

The term "5- or 6-membered heterocyclic ring" represents those 5- and 6-membered heterocycles with 1- or 2-heteroatoms selected from oxygen, nitrogen and sulfur. Exemplary of such heterocycles is imidazole, furan, thiazole, pyrazole, pyridine and the like.

In the Formulae I, II and III compounds, there are several assymetric centers which lead to the existence of optical isomers for such compounds. For each of the assymetric centers of the various amino acids which make up these cyclic hexapeptides, both the D and L configurations are intended to be encompassed.

The following are representative cyclic hexapeptide analogs of somatostatin which can be respectively formed from the Formula I, II and III compounds above:

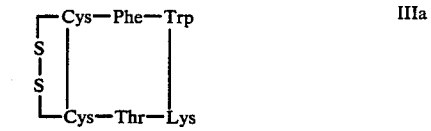

Preferred Formula I compounds are:
(1) Cyclo-(N-Me-Ala-Tyr-D-Trp-Lys-Thr-Phe)
(2) Cyclo-(N-Me-Ala-Phe-D-Trp-Lys-Thr-Phe)
(3) Cyclo-(N-Me-Ala-Phe-L-Trp-Lys-Thr-Phe)
(4) Cyclo-(N-Me-Ala-Phe-D-Trp-Lys-Thr-p-Cl-Phe)
(5) Cyclo-(N-Me-Ala-Phe-D-5-F-Trp-Lys-Thr-Phe)
(6) Cyclo-(N-Me-Ala-Phe-L-5-F-Trp-Lys-Thr-Phe)
(7) Cyclo-(N-Me-Ala-Phe-D-Trp-Lys-Ser-Phe)
(8) Cyclo-(N-Me-Ala-Tyr-D-Trp-Lys-Val-Phe)
(9) Cyclo-(N-Me-Ala-Tyr-D-Trp-Lys-Val-Trp)
(10) Cyclo-(N-Me-Ala-Tyr-L-Trp-Lys-Val-Phe)
(11) Cyclo-(Ser-Ala-N-Me-Phe-His-D-Trp-Lys)

Preferred Formula II compounds are:
(12) Cyclo-(Pro-Tyr-D-Trp-Lys-Thr-Phe)
(13) Cyclo-(Pro-Phe-D-Trp-Lys-Thr-Phe)
(14) Cyclo-(Pro-Phe-L-Trp-Lys-Thr-Phe)
(15) Cyclo-(Pro-Phe-D-Trp-Lys-Thr-p-Cl-Phe)

(16) Cyclo-(Pro-Phe-D-5-F-Trp-Lys-Thr-Phe)
(17) Cyclo-(Pro-Phe-L-5-F-Trp-Lys-Thr-Phe)
(18) Cyclo-(Pro-Phe-D-Trp-Lys-Ser-Phe)

Preferred Formula III compounds are:

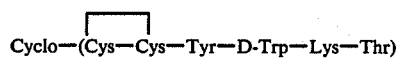 (19)

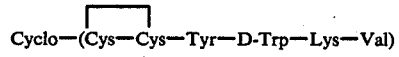 (20)

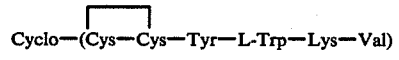 (21)

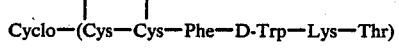 (22)

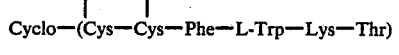 (23)

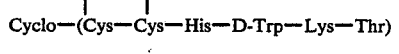 (24)

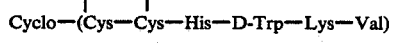 (25)

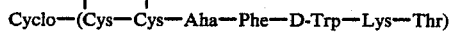 (26)

Preferred Formula IV compounds are:

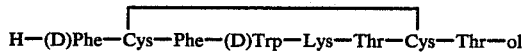 (27)

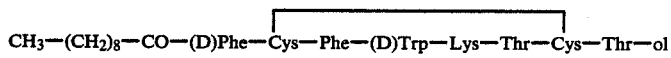 (28)

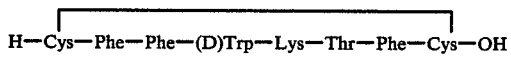 (29)

 (30)

In the instant application several abbreviated designations are used for the amino acid components and the meaning of these abbreviated designations are given below:

| Abbreviated Designation | Amino Acid |
|---|---|
| Lys | L-lysine |
| Phe | L-phenylalanine |
| Trp | L-tryptophan |
| D-Trp | D-tryptophan |
| Thr | L-threonine |
| Aha | 7-aminoheptanoic acid |
| Tyr | L-tyrosine |
| Val | L-valine |
| Abu | L-a-aminobutyric acid |
| Ser | L-serine |
| Asn | L-asparagine |
| Pro | L-proline |
| Asu | D- or L-aminosuberic acid |
| Cys | L-cysteine |
| Gaba | α-Amino-butyric acid |
| Thr-ol | Reduced carboxylate of Thr |

Local treatment of inflammatory and allergic conditions with the Formula I, II, III, IV and V compounds is accomplished by providing the compounds in the form of a suitable pharmaceutical composition containing a Formula I, II, III, IV or V compound or mixtures thereof as the active ingredient.

Thus, suitable pharmaceutical compositions containing the active ingredient can be in the form of creams, ointments, jellies, solutions, suspensions, sprays, eye drops, dispersible powders, and the like, and can be used to effectively treat warm blooded animals such as mice, rats, horses, dogs, cats, cattle, and the like, and humans. Such pharmaceutical compositions, in addition to an effective dosage amount of the active ingredient, typically include pharmaceutically acceptable carrier, adjuvants and vehicles.

For example, aqueous suspensions can be used containing the active ingredient in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate. The aqueous suspensions may also contain one or more preservatives, for example, ethyl, or n-propyl, p-hydroxybenzoate, one or more coloring agents, one or more flavoring agents, and one or more sweetening agents, such as sucrose or saccharin.

Oily suspension can also be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives can be employed. Suitable dispersing or wetting agents and suspending agents are exemplified by those already mentioned above. Additional excipients, for example, sweetening, flavoring and coloring agents, may also be included.

The pharmaceutical composition of the present invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

The pharmaceutical compositions can be in the form of an oleagenous suspension. This suspension can be formulated according to the known art using suitable dispersing or wetting agents and suspending agents which have been mentioned above.

For topical use, creams, ointments, jellies, solutions or suspensions, etc., containing the anti-inflammatory agents are employed.

The amount of active ingredient; i.e. the Formula I, II, III, IV, or V compound or mixtures thereof, for use in the present compositions will vary depending, for example, the condition being treated and the size and kind of mammal. Generally speaking, the active ingredient can be employed in any amount known to be an anti-inflammatory amount, as well as at doses one-fifth to one-third lower than the usual amounts for multiple daily applications.

For humans, typical effective anti-inflammatory amounts of active ingredient for use in unit dose compositions of the invention are about 0.001% to about 2.0% by weight of the composition, preferably about 0.1% to about 0.5% by weight of the composition. However, greater amounts can be employed if desired or prescribed.

DETAILED DESCRIPTION OF THE INVENTION

Protocol:

The assay method employed to test the Formula I, II, III, IV and V compounds as local anti-inflammatory agents is a modification of the method described by S. L. Steelman, et al. [Steroids, 1, 163 (1963)] as follows:

ASSAY METHOD

Male rats (Charles River-CD) of about 150–160 grams in weight were subcutaneously implanted in the abdominal area with two pellets each. Five animals were used per group. The pellets used were preweighed and all used in a given assay were ±1 mg from one another. The compounds were dissolved in absolute ethanol and the indicated dose applied to each pellet in 0.2 ml. The alcohol was removed in vacuo overnight. Just prior to implantation, each pellet was moistened with 0.2 ml of 0.9% saline containing 1 mg each of penicillin and streptomycin. After seven days, the pellets were dissected out together with adhering granulomatous tissue. After drying in a vacuum oven overnight at 60°–65° C., the pellets were weighed. The difference in weight between the original pellet weight and the implanted pellet weight was used as a measure of cellular proliferation (granuloma). The lower the net weight, the more anti-inflammatory activity.

ASSAY 1

Following the procedure of the Assay Method described above, somatostatin (SRIF) was tested for its anti-inflammatory activity. The structure of somatostatin is:

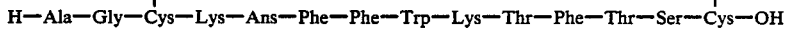

H—Ala—Gly—Cys—Lys—Ans—Phe—Phe—Trp—Lys—Thr—Phe—Thr—Ser—Cys—OH

Six animals per group were used in this test and the results obtained are shown in Table I below wherein hydrocortisone was used as a positive control:

TABLE I

| Group | Dose/Pellet | Granulosimer Net weight |
|---|---|---|
| Control | — | 35 ± 3 mg |
| Hydrocortisone | 300 mcg | 24 ± 2 mg* |
| SRIF | 1500 mcg | 25 ± 1 mg** |

± 2 S.E. of mean
*vs. Control p = <0.02
**vs. Control p = <0.01

The results in Table I above clearly show that somatostatin (SRIF) is an effective anti-inflammatory agent and that compounds having somatostatin-like activity should also be useful as anti-inflammatory agents.

ASSAY 2

The results obtained following the Assay Method described above using Compound 8 of Formula I are shown below in Table II wherein hydrocortisone was used as a positive control.

TABLE II

| Group | Dose/Pellet | Body Wt. Change (gm) | Net weight of Pellets (mg) |
|---|---|---|---|
| Control | — | +43 | 39 ± 2.7 |
| Hydrocortisone | 200 mcg. | +44 | 34 ± 2.5 |
| Hydrocortisone | 1000 mcg. | +41 | 29 ± 2.1* |
| Compound 8 of Formula I | 10 mcg. | +43 | 39 ± 2.9 |
| Compound 8 of Formula I | 100 mcg. | +40 | 30 ± 2.4** |

± S.E. of mean
*vs Control p = <0.01
**vs Control p = <0.05

Table II above reveals that Compound 8 of Formula I exhibits significant activity at doses of 100–200 micrograms per pellet. Furthermore, no significant changes in body weights during the treatment period were noted in this Assay.

ASSAY 3

Following the procedure described above for Assau 1, additional tests were conducted except that the compounds were administered subcutaneously as saline injections. The tests were carried out on six animals per group and the results obtained are shown below in Table III.

TABLE III

| Group | Daily Dose | Avg. body wt change (gm) | Avg. Thymus wt. (mg) | Avg. Adrenal wt. (mg) | Avg. Granuloma wt. (mg) |
|---|---|---|---|---|---|
| Control | — | +35 ± 2 | 552 ± 45 | 44 ± 1 | 28 ± 3 |
| Hydrocortisone | 1.0 mg | +22 ± 3** | 201 ± 20** | 36 ± 3* | 22 ± 1 |
| Hydrocortisone | 4.0 mg | −17 ± 2** | 41 ± 3** | 23 ± 1** | 19 ± 1** |
| Compound 8 of Formula I | 50 mcg | +38 ± 3 | 576 ± 14 | 43 ± 2 | 27 ± 3 |
| Compound 8 of Formula I | 200 mcg | +35 ± 2 | 571 ± 26 | 36 ± 2** | 29 ± 2 |

± S.E. of mean
*p = <0.05
**p = <0.01

The results set forth in Table III above reveal that Compound 8 of Formula I exhibited no anti-inflammatory activity when administered subcutaneously at a total dose of 1.4 mg (0.2 mg×7). The only noticeable biological effect noted with respect to Compound 8 of Formula I was a slight decrease in the adrenal weight of the animals tested. It will be noted that hydrocortisone exhibited its typical activity.

Comparing the results shown in Tables II and III above, it can be seen that Compound 8 of Formula I clearly exhibits anti-inflammatory activity when administered locally; i.e., topically, but no anti-inflammatory activity when administered systemically, i.e., subcutaneously.

ASSAY 4

Following the same procedure as described above for Assay 1, additional compounds were tested for local; i.e., topical, anti-inflammatory activity. The results obtained and the relative activity of these additional compounds compared to Compound 8 of Formula I are set forth in Table IV below wherein the activity values of the compounds tested represent an arbitrary assignment of the order of magnitude of the compounds based upon the compound exhibiting the lowest potency. In Table IV, the potency of each compound tested relative to that of somatostatin is also shown, the somatostatin (SRIF) potency being assigned a value of 1 and based upon its inhibition of growth hormone, insulin and glucogen secretion.

TABLE IV

| Compound/Formula | Potency Relative to Somatostatin (SRIF) | Local Anti-inflammatory Activity |
|---|---|---|
| 8/I | 50-100 | 3+ |
| 26/III | 2-3 | 1+ |
| 13/II | 6 | 1-2+ |
| 9/I | 20-35 | 3+ |
| 10/I | 50 | 3+ |
| 11/I | 200 | 4+ |

The results shown in Table IV above indicate that there appears to be a positive relationship between somatostatin (SRIF) potency and local anti-inflammatory activity.

What is claimed:

1. A method of locally treating inflammatory and allergic conditions comprising applying to the area to be treated an anti-inflammatory and anti-allergically effective amount of a compound having the Formulae:

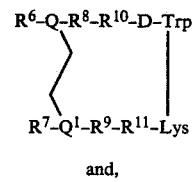

IV and,

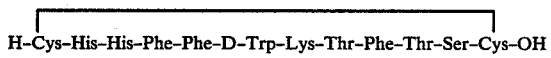

V

H—Cys—His—His—Phe—Phe—D-Trp—Lys—Thr—Phe—Thr—Ser—Cys—OH wherein in the compound of Formula IV:
R⁶ is D-Phe; CH₃(CH₂)₈CO-D-Phe; or is absent;
R⁷ is Thr or is absent;
R⁸ and R⁹ can each independently be Phe or be absent;
R¹⁰ is Phe or Tyr;
R¹¹ is Val or Thr;
Q is Cys or Asn; and,
Q¹ is Cys or, when Q, R⁶ and R⁷ are absent, Gaba.

2. The method of claim 1 wherein said Formula IV compound is a member of the group:

H—(D)Phe—Cys—Phe—(D)Trp—Lys—Thr—Cys—Thr—ol;

CH₃—(CH₂)₈—CO—(D)Phe—Cys—Phe—(D)Trp—Lys—Thr—Cys—Thr—ol;

H—Cys—Phe—Phe—(D)Trp—Lys—Thr—Phe—Cys—OH; and,

Cyclo—(Asn—Phe—Phe—(D)Trp—Lys—Thr—Phe—Gaba).

3. A method of locally treating atopic eye diseases comprising applying to the area to be treated an anti-atopically effective amount of a compound having the Formulae:

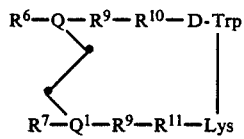
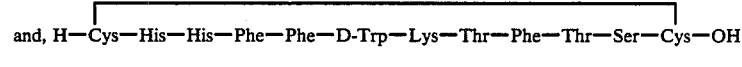

wherein in the compound of Formula IV:
$R^6$ is D-Phe; $CH_3(CH_2)_8CO$-D-Phe; or is absent;
$R^7$ is Thr or is absent;
$R^8$ and $R^9$ can each independently be Phe or be absent;

$R^{10}$ is Phe or Tyr;

$R^{11}$ is Val or Thr;
Q is Cys or Asn; and,
$Q^1$ is Cys or, when Q, $R^6$ and $R^7$ are absent, Gaba.

4. The method of claim 3 wherein said Formula IV compound is a member of the group:

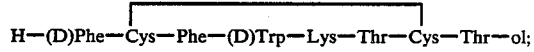

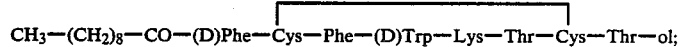

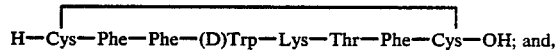

Cyclo—(Asn—Phe—Phe—(D)Trp—Lys—Thr—Phe—Gaba).

* * * * *